United States Patent [19]

Boschelli et al.

[11] Patent Number: 5,424,329
[45] Date of Patent: Jun. 13, 1995

[54] INDOLE-2-CARBOXAMIDES AS INHIBITORS OF CELL ADHESION

[75] Inventors: Diane H. Boschelli, Plymouth; David T. Connor; Paul C. Unangst, both of Ann Arbor, all of Mich.

[73] Assignee: Warner-Lambert Company, Morris Plains, N.J.

[21] Appl. No.: 108,952

[22] Filed: Aug. 18, 1993

[51] Int. Cl.$^6$ .............................................. A61K 31/40
[52] U.S. Cl. .................................... 514/418; 514/419; 548/483; 548/484
[58] Field of Search .................................. 514/418, 419

[56] References Cited

U.S. PATENT DOCUMENTS

| | | | |
|---|---|---|---|
| 4,675,332 | 6/1987 | Connor et al. | 514/381 |
| 4,803,198 | 2/1989 | Ohlendorf | 514/418 |
| 5,051,442 | 9/1991 | Salituro et al. | 514/419 |
| 5,081,138 | 1/1992 | Gillard et al. | 514/418 |
| 5,095,031 | 3/1992 | Brooks et al. | 514/419 |
| 5,288,743 | 2/1994 | Brooks et al. | 514/418 |

FOREIGN PATENT DOCUMENTS

| | | | |
|---|---|---|---|
| 396124 | 11/1990 | European Pat. Off. | |
| 530907 | 3/1993 | European Pat. Off. | 548/484 |

OTHER PUBLICATIONS

Kavanaugh et al. Arthritis & Rheumatism vol. 37 No. 7 (Jul. 1994) pp. 992–999.
Springer *Nature*, vol. 346, pp. 425–434, 1990.
McEver *Thrombosis and Haemostasis*, vol. 65, No. 3, pp. 223–228, 1991.
Wardlaw *Clinical and Experimental Allergy*, vol. 20, pp. 619–626, 1990.
Jutila et al. *Transplantation*, vol. 48, No. 5, pp. 727–731, 1989.
Vadas et al. *Biochemical Pharm.*, vol. 40, No. 8, pp. 1683–1687, 1990.
Bevilacqua et al *Proc. Natl. Acad. Sci. USA*, vol. 84, pp. 9238–9242, 1987.
Smith et al *J. Clin. Invest.*, vol. 82, pp. 1746–1756, 1988.
Hakkert et al *Blood*, vol. 78, No. 10, pp. 2721–2726, 1991.
Mitsuya et al. *Proc. Natl. Acad. Sci. USA*, vol. 83, pp. 1911–1915, 1986.
Pober et al *J. Immun.*, 137:1893, 1986.

*Primary Examiner*—Donald G. Daus
*Attorney, Agent, or Firm*—Ronald A. Daignault; Charles W. Ashbrook

[57] ABSTRACT

3-Substituted-indole-2-carboxamides are described as agents which inhibit leukocyte adherence to vascular endothelium and, as such, are effective therapeutic agents for treating inflammatory diseases. Certain of these compounds are novel and methods of manufacture are also described.

Certain of the indole-2-carboxamides also inhibit the activation of human immunodeficiency virus (HIV), latent in infected humans.

6 Claims, No Drawings

INDOLE-2-CARBOXAMIDES AS INHIBITORS OF CELL ADHESION

The present invention is for the use of certain 3-substituted-indole-2-carboxamides, and pharmaceutically acceptable acid addition salts thereof, to prevent the adhesion of leukocytes to endothelial cells. Leukocyte adherence to vascular endothelium is integral to the pathogenesis of inflammation. The adhesion process precedes transendothelial migration of leukocytes into surrounding tissue and ensuing tissue damage. Compounds that can block this initial adhesive interaction are expected to have efficacy in the treatment of inflammatory diseases such as rheumatoid arthritis, asthma, and psoriasis. Other indications would include but are not limited to adult respiratory distress syndrome, reperfusion injury, ischemia, ulcerative colitis, vasculitides, atherosclerosis, inflammatory bowel disease, and tumor metastases.

Adhesion receptors are organized into three main families: the selectins, the immunoglobulin superfamily, and the integrins (Nature 1990;346:426). Members of all three classes are involved in mediating leukocyte adhesion during inflammation (for reviews of this area see: Thrombosis and Hemostasis 1991;65(3):223, Clinical and Experimental Allergy 1990;20:619, Transplantation 1989;48:727, Biochemical Pharm. 1990;40(8):1683). Endothelial leukocyte adhesion molecule-1 (ELAM-1 or E-selectin) is a member of the selectin family of glycoproteins that promote cell-cell adhesion. ELAM-1 is reported to be maximally expressed on the surface of endothelial cells 4 hours after stimulation of the endothelial cells with cytokines, such as interleukin-1 (In-1) or tumor necrosis factor-α (TNF-α) or other inflammatory mediators, such as lipopolysaccharide (LPS) (PRO, Nat. Acad. Sci. 1987;84:9238).

Intercellular adhesion molecule-1 (ICAM-1) is a member of the immunoglobulin superfamily. It is also up-regulated with maximum expression occurring 12 to 24 hours after stimulus. It has been shown that 4 hours after the endothelial cells are stimulated with an inflammatory mediator, both ELAM-1 and ICAM-1 are present on the cell surface (J. Clin. Invest. 1988;82:1746 and J. Immun. 1986;137:1893, Blood 1991;78:2721).

The 3-substituted-indole-2-carboxamides of the present invention have been shown in an in vitro assay to prevent the adhesion of neutrophils to human umbilical vein endothelial cells (HUVECS) stimulated with TNF-α.

The present invention also relates to a series of 3-substituted-indole-2-carboxamides for treating humans infected with human immunodeficiency virus (HIV) by inhibiting the activation of HIV, latent in infected humans.

The pathogenesis of the human immunodeficiency virus (HIV) is complicated and as of yet not completely understood. The virus life cycle has theoretically been divided into afferent and efferent components. Virus binding, fusion, reverse transcription, and finally integration are among those events which encompass the afferent component of the life cycle. It is the afferent component of the HIV life cycle which is responsible for primary infection of HIV in an individual, generally followed by a burst of viraemia with or without clinical symptoms.

Many therapeutic strategies have been developed and targeted for intervention during the afferent events. See for example, Mitsuya H, Broder S, "Inhibition of the In Vitro Infectivity and Cytopathic Effect on Human T-lymphotropic Virus Type III/lymphadenopathy Virus-associated Virus (HTLV-III/LAV) by 2′, 3′-Dideoxynucleosides," Proc. Natl. Acad. Sci. (USA) 1986;83:1911–1915.

Whereas different stages of the afferent component offer the potential for effective therapeutic intervention, it has become increasingly apparent that intervention solely at these points is insufficient. After becoming infected with HIV and the disease progresses through the afferent stages, an individual experiences a prolonged period of clinical latency which may extend for several years and the individual remains in good health. At this point in time, low to absent levels of viraemia and virus replication in peripheral blood cells are achieved. At a later point, however, the disease eventually progresses to life-threatening immunosuppression (AIDS) for which there remains no cure. These later events are the clinical manifestations of the efferent stages of HIV infection.

The efferent component of the HIV life cycle includes those events necessary for the HIV provirus to successfully transcribe, translate, assemble, and produce virions. Onset of the events necessary for HIV-infected cells to progress from an asymptomatic, non-HIV expressive stage to a symptomatic, HIV expressive stage is referred to as activation. Presently, the efferent component and the cellular basis for activation is not completely understood. Nevertheless, if novel therapeutic agents and strategies are developed and implemented during the clinically asymptomatic phase to fight the progression toward AIDS, some hope may be afforded the estimated one million infected, but clinically latent, individuals.

While 3-substituted-indole-2-carboxamides have already been described, the present invention includes certain novel compounds not previously described and, more importantly, includes novel therapeutic uses for those already known compounds.

SUMMARY OF THE INVENTION

Accordingly, the present invention is for the use of a compound of the formula (I) to inhibit the adhesion of leukocytes to stimulated human endothelial cells, thereby providing for the treatment of inflammatory diseases:

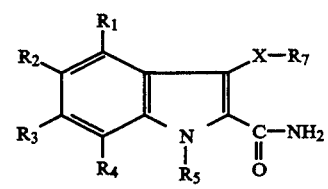

wherein $R_1$, $R_2$, $R_3$, and $R_4$ are each independently hydrogen, hydroxy, halogen, lower alkyl, lower alkoxy, benzyloxy, nitro, or —$NR_8R_9$, in which $R_8$ and $R_9$ are each independently hydrogen or lower alkyl;

$R_5$ is hydrogen, lower alkyl, phenyl, benzyl, or —$CH_2OR_{10}$ in which $R_{10}$ is lower alkyl;

$R_7$ is lower alkyl, phenyl, or benzyl;

X is $S(O)_n$ or $NR_{11}$ in which n is 0, 1, or 2 and $R_{11}$ is hydrogen, lower alkyl, phenyl, or benzyl, or a pharmaceutically acceptable acid addition salt thereof, excluding 5-methoxy-3-(methylthio)-1H-indole-2-carboxamide, and with the proviso that $R_5$ is benzyl only when X is $NR_{11}$.

Preferred are compounds wherein $R_1$, $R_3$, and $R_4$ are hydrogen;

$R_2$ is hydroxy, lower alkoxy, or benzyloxy;

$R_5$ is hydrogen, lower alkyl, or phenyl; and $R_7$ is lower alkyl.

Particularly, the present invention is the use ore the following compounds in their free form or as pharmaceutically acceptable acid addition salts to treat inflammatory diseases by administering an effective amount in unit dosage form of:

5-methoxy-1-methyl-3-(methylthio)-1H-indole-2-carboxamide, 3-(diethylamino)-5-methoxy-1H-indole-2-carboxamide, 1-methyl-3-[(1-methylethyl)thio]-5-(phenylmethoxy)-1H-indole-2-carboxamide, 5-methoxy-1-methyl-3-[(1-methylethyl)thio]1H-indole-2-carboxamide, and 5-hydroxy-1-methyl-3-[(1-methylethyl)thio]1H-indole-2-carboxamide.

A second aspect of the present invention is the use of a compound of the formula (II) to inhibit the adhesion of leukocytes to stimulated human endothelial cells, thereby providing for the treatment of inflammatory diseases:

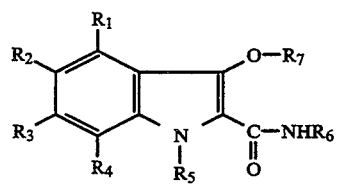

II wherein $R_1$, $R_2$, $R_3$, and $R_4$ are each independently hydrogen, hydroxy, halogen, lower alkyl, lower alkoxy, benzyloxy, nitro, or $-NR_8R_9$, in which $R_8$ and $R_9$ are each independently hydrogen or lower alkyl;

$R_5$ is hydrogen, lower alkyl, phenyl, or $-CH_2OR_{10}$ in which $R_{10}$ is lower alkyl;

$R_6$ is hydrogen, lower alkyl, or benzyl;

$R_7$ is lower alkyl, phenyl, or benzyl, or a pharmaceutically acceptable acid addition salt thereof.

Preferred compounds wherein $R_1$, $R_3$, and $R_4$ are hydrogen, $R_2$ is hydroxy or lower alkoxy;

$R_5$ is hydrogen, lower alkyl, or phenyl;

$R_6$ is hydrogen; and $R_7$ is lower alkyl.

Particularly preferred are the following compounds:

5-methoxy-1-methyl-3-(1-methylethoxy)-1H-indole-2-carboxamide, 5-hydroxy-1-methyl-3-(1-methylethoxy)-1H-indole-2-carboxamide, 5-methoxy-3-(1-methylethoxy)-1-phenyl-1H-indole-2-carboxamide, 5-methoxy-3-(1-methylethoxy)-1H-indole-2-carboxamide, 3-ethoxy-5-methoxy-1-phenyl-1H-indole-2-carboxamide, 5-methoxy-3-(1-methylethoxy)-1-methoxymethyl-1H-indole-2-carboxamide, and 1-ethoxymethyl-5-methoxy-3-(1-methylethoxy)-1H-indole-2-carboxamide.

A third aspect of the present invention is the use of a compound of the formula (III) to treat humans infected with HIV, thereby providing for the treatment of AIDS:

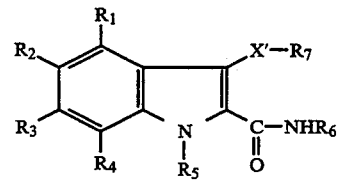

III wherein $R_1$, $R_2$, $R_3$, and $R_4$ are each independently hydrogen, hydroxy, halogen, lower alkyl, lower alkoxy, benzyloxy, nitro, or $-NR_8R_9$ in which $R_8$ and $R_9$ are each independently hydrogen or lower alkyl;

$R_5$ is hydrogen, lower alkyl, phenyl, benzyl, or $-CH_2OR_{10}$ in which $R_{10}$ is lower alkyl;

$R_6$ is hydrogen, alkyl, or benzyl;

$R_7$ is lower alkyl, phenyl, or benzyl;

$X'$ is O, $S(O)_n$ or $NR_{11}$ in which n is 0, 1, or 2 and $R_{11}$ is hydrogen, lower alkyl, phenyl, or benzyl, or a pharmaceutically acceptable acid addition salt thereof, with the proviso that $R_5$ is hydrogen only when $X'$ is $NR_{11}$.

Particularly preferred is the use of 5-methoxy-1-methyl-3-(1-methylethoxy)-1H-indole-2-carboxamide or a pharmaceutically acceptable acid addition salt to treat AIDS by administering an effective amount of the compound in unit dosage form.

A fourth aspect of the present invention are novel compounds of the formula (IV)

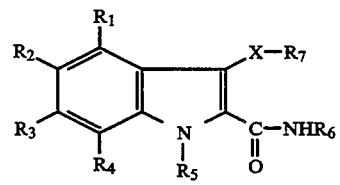

IV wherein $R_1$, $R_2$, $R_3$, and $R_4$ are each independently hydrogen, hydroxy, halogen, lower alkyl, lower alkoxy, benzyloxy, nitro, or $-NR_8R_9$, in which $R_8$ and $R_9$ are each independently hydrogen or lower alkyl;

$R_5$ is lower alkyl, phenyl, or $-CH_2OR_{10}$ in which $R_{10}$ is lower alkyl;

$R_6$ is hydrogen or benzyl;

$R_7$ is lower alkyl, phenyl, or benzyl;

X is $S(O)_n$ or $NR_{11}$ in which n is 0, 1, or 2 and $R_{11}$ is hydrogen, lower alkyl, phenyl, or benzyl, or a pharmaceutically acceptable acid addition salt thereof.

Preferred are compounds of Formula IV wherein $R_2$ is hydroxy, lower alkoxy, or benzyloxy;

$R_5$ is lower alkyl or phenyl; and $R_7$ is lower alkyl.

Particularly valuable are:

5-methoxy-1-methyl-3-(methylthio)-1H-indole2-carboxamide, 1-methyl-3-[(1-methylethyl)thio]-5-(phenylmethoxy)-1H-indole-2-carboxamide, 5-methoxy-1-methyl-3-[(1-methylethyl)thio]-1H-indole-2-carboxamide, and 5-hydroxy-1-methyl-3-[(1-methylethyl)thio]-1H-indole-2-carboxamide.

A fifth aspect of the present invention are novel compounds within the compounds of Formula II. These are 5-methoxy-3-(1-methylethoxy)-1-methoxymethyl-1H-indole-2-carboxamide and 1-ethoxymethyl-5-methoxy-3-(1-methylethoxy)-1H-indole-2-carboxamide, or a pharmaceutically acceptable acid addition salt thereof and pharmaceutical compositions comprising an effective amount of one of these compounds with a pharmaceutically acceptable carrier.

Finally, the present invention includes pharmaceutical compositions comprising a therapeutically effective amount of a compound of the Formula IV above, its preferred and particularly valuable embodiments, together with a pharmaceutically acceptable carrier.

DETAILED DESCRIPTION

The terms used in defining the compounds of Formulas I, II, III, and IV, and the more particular compounds of the present invention are defined as follows:

Lower alkyl and lower alkoxy mean a straight or branched alkyl or alkoxy group having 1 to 4 carbon atoms and includes, for example, methyl, ethyl, propyl, i-propyl, or otherwise referred to as (methyl)ethyl, and t-butyl or otherwise referred to as 1,1-(dimethyl)methyl, and correspondingly, for example, methoxy, ethoxy, i-propoxy, or otherwise referred to as 1-(methyl)ethoxy and the like.

Halogen includes fluorine, chlorine, bromine, or iodine.

The compounds of the Formulas I through IV are capable of further forming pharmaceutically acceptable acid addition salts. All of these forms are within the scope of the present invention.

Pharmaceutically acceptable acid addition salts of the compounds of Formulas I through IV include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine (see, for example, Berge SM, et al., "Pharmaceutical Salts," *Journal of Pharmaceutical Science* 1977; 66: 1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

In determining when a cell adhesion inhibitor or inhibitor of HIV activation is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formulas I, II, or III or a pharmacologically acceptable salt thereof to achieve a therapeutic effect will, of course, vary both with the particular compound, the route of administration, the mammal under treatment, and the particular disorder of disease concerned. A suitable dose of a compound of Formulas I, II, or III or a pharmacologically acceptable salt thereof for a mammal suffering from, or likely to suffer from any condition as described hereinbefore is 0.1 µg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 µg of the compound per kilogram, typically about 0.1 µg/kg.

In the case of oral dosing for the treatment or prophylaxis of arthritis or inflammation in general, due to any course, a suitable dose of a compound of Formulas I or II or a physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formulas I through IV or a pharmacologically acceptable acid addition thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention, particularly those of Formulas I or II, as inhibitors of leukocyte adherence to vascular endothelium and thus in treating inflammatory-related diseases or conditions may be demonstrated by their effectiveness in various standard test procedures. A description of each procedure and exemplary test results follows.

METHOD FOR DETERMINING THE INHIBITION OF HUMAN NEUTROPHIL ADHESION TO TNF-α, IL-1α, AND LPS-STIMULATED HUMAN UMBILICAL VEIN ENDOTHELIAL CELLS BY 3-SUBSTITUTED-INDOLE-2-CARBOXAMIDES

Isolation of Neutrophils

Neutrophils were isolated from anticoagulant-treated venous blood obtained from healthy human volunteers according to the method of Ferrante and Thong (*J. Immunol. Methods* 1978;24:389–393). The cell preparations consisted of greater than 98% neutrophils.

Endothelial Cell Culture

Second passage human umbilical vein endothelial cells (HUVEC) (Clonetics, San Diego, Calif.) were seeded into Falcon 24-well cell culture plates (Becton Dickinson, Lincoln Park, N.J.) at approximately $2 \times 10^4$ cells per well. The cells were grown to confluent monolayers in endothelial basal medium (EBM, Clonetics) supplemented with 5% fetal calf serum (Hyclone Laboratories, Logan, Utah), 10 ng/mL EGF, 1μg/mL hydrocortisone, 0.4% bovine brain extract (Clonetics) in 5% $CO_2$ at 37° C.

Neutrophil Adhesion

Neutrophils ($30 \times 10^6$) were labeled for 60 minutes at 37° C. with 100 μCi $Na^{51}CrO_4$ (ICN Biomedicals, Costa Mesa, Calif.) in 2.0 mL $Ca^{2+}$-and $Mg^{2+}$-free Hanks' balanced salt solution (HBSS, GIBCO Laboratories, Grand Island, N.Y.). The cells were washed two times in HBSS and suspended in unsupplemented EBM.

Stimulation of HUVEC with tumor necrosis factor-α (TNF-α) (Genzyme, Cambridge, Mass.), interleukin (IL-1α) (Genzyme) or *E. coli* 0111:B4 lipopolysaccharide (LPS) (Sigma) in the presence or absence of drug was initiated 4 hours prior to the addition of neutrophils. The suspension medium was unsupplemented EBM or supplemented EBM for studies with cytokines or LPS, respectively. Such treatment has been shown to promote maximal expression of the endothelial cell-leukocyte adhesion molecule ELAM-1 as well as expression of ICAM-1 (*J. Immunol.* 1986;137:1893; *Proc. Natl. Acad. Sci. USA* 1987:9238). Immediately prior to addition of $^{51}Cr$-labeled neutrophils to the HUVEC monolayers, the cultures were washed with 1 mL unsupplemented media to remove stimulus and/or drug. Neutrophils ($5 \times 10^5$) were then added to the HUVEC in 0.5 mL unsupplemented media and incubated at 37° C. for 30 minutes. Nonadherent neutrophils were removed by aspiration. Following an additional wash, adherent neutrophils were lysed with 0.5 mL 1N $NH_4OH$ overnight at 37° C. Lysates were collected and the radioactivity in each well was determined by gamma ray spectroscopy.

An alternate method for determining adhesion is also used and described as follows.

MODIFIED METHOD FOR DETERMINING THE INHIBITION OF HUMAN NEUTROPHIL ADHESION TO TNF-α, IL-1α, AND LPS STIMULATED HI/MAN UMBILICAL VEIN ENDOTHELIAL CELLS BY 3-SUBSTITUTED-INDOLE-2-CARBOXAMIDES

Cell Culture

Second passage HUVEC (Clonetics Corporation, San Diego, Calif., CC-2617) were seeded into Corning (Corning glass works, Corning, N.Y.) 96-well cell culture plates at approximately $5 \times 10^3$ cells/well and grown to confluency in supplemented endothelial basal medium (EBM, MCDB-131, Clonetics, 10 ng/mL EGF, 1 μg/mL hydrocortisone, 0.4% bovine brain extract, 5% Fetal Bovine Serum). One day prior to running the assay, typically 3 days postseeding, the cultures were re-fed with 0.2 mL/well supplemented EBM (S-EBM).

Preparation of Test Compounds

Test compounds were prepared as 10 mL stock solutions at a concentration of 1.0 mM. The compounds were initially solubilized in 0.1 mL DMSO followed by the addition of 9.9 mL S-EBM. The drug preparations were then diluted in one step to a concentration of 66.6 μM. Solubilizations and dilutions were performed in polystyrene containers.

Isolation of Human Neutrophils

Human neutrophils were isolated from anticoagulant-treated venous blood obtained from healthy volunteers according to the method of Ferrante and Thong, *J. Immunol. Methods* 1978;24:389–393. The cell preparations consisted of greater than 98% neutrophils.

Stimulation of HUVEC

Recombinant human tumor necrosis factor-α (TNF, Genzyme, Boston, Mass., code TNF-H) was prepared at 400 U/mL in S-EBM. Stock TNF was prepared to 20,000 U/mL in Delbecco's phosphate buffered saline (PBS, Gibco, Grand Island, N.Y.) plus 0.1% BSA and stored at −70° C. HUVEC were washed one time with 0.2 mL warm unsupplemented EBM and then stimulated for 4 hours at 37° C. with 200 U/mL TNF in the presence of 33.3 μM test compound. This was accomplished by adding 0.1 mL of 400 U/mL TNF and 0.1 mL 66.6 μM test compound. These additions were done slowly as to not disrupt the HUVEC monolayer. Each compound was tested in six wells. Unstimulated (vehicle control) and TNF-stimulated without test compound treatments were also run in each plate.

Labeling of Neutrophils

One hour prior to adding the neutrophils to the HUVEC, neutrophils ($5 \times 10^6$/mL) were labeled for 30 minutes at 37° C. with 5 μM calcein-AM (Molecular Probes, Eugene, Oreg.) in Hanks' balanced salt solution plus 0.45% BSA. Stock calcein was prepared to 5 mM in anhydrous DMSO and stored desiccated at −20° C. At the end of the incubation the cells were washed two times in cold HBSS and resuspended to a final concentration of $1 \times 10^6$ cells/mL in unsupplemented EBM.

Addition of Neutrophils to HUVEC

At the end of the 4-hour stimulation and immediately prior to the addition of the neutrophils to the HUVEC monolayer, the plates were washed with 0.2 mL warm unsupplemented EBM to remove TNF and drug. Neutrophils ($1 \times 10^5$ cells) were slowly added to each of the treated wells and incubated for 30 minutes at 37° C. At the end of the incubation the plates were washed two times with 0.2 mL warm unsupplemented EBM followed by a final addition of 0.1 mL for plate scanning.

Determination of Relative Fluorescence

The relative fluorescence was determined using a Millipore Cytofluor 2300 system (excitation=480, emission=530, sensitivity=4). Each file was saved on disk as a comma separated value (.CSV) file for import into a spreadsheet.

Calculations

The assay was considered valid if the TNF-stimulation of the HUVEC resulted in a 300% increase in neutrophil adherence over adherence to unstimulated HUVEC. Results were expressed as means of percent inhibition of TNF-stimulated adherence. A Quattro Pro (Borland, Scotts Valley, Calif.) spreadsheet has been programmed to accept the raw data and perform all necessary calculations.

$$\% \text{ Inhibition} = 100 - \left[ \frac{\text{stimulated adherence}_{(drug)} - \text{unstimulated adherence}}{\text{stimulated adherence}_{(control)} - \text{unstimulated adherence}} \right] \times 100$$

Some of these compounds which exhibited inhibitory activity of 50% or greater at 33.3 μM were retested at concentrations of 33.3 μM, 10.0 μM, 3.3 μM, and 1.0 μM to determine IC$_{50}$ values. Linear regression analysis of the means of the inhibition values were used to determine the IC$_{50}$.

The results obtained with certain compounds of the present invention are shown in Table I.

TABLE I

| Inhibition of Adhesion by Indole Carboxamides | |
| --- | --- |
| Example | Adhesion (% inhibition at given μM or IC$_{50}$, μM) |
| 1 | 10 |
| 6 | 72 @ 33 μM |
| 15 | 7 |
| 16 | 35 @ 100 μM[a] |
| 18 | 8 |
| 19 | 13 @ 33 μM |
| 20 | 27 @ 33 μM |
| 23 | 15 @ 33 μM |

TABLE I-continued

| Inhibition of Adhesion by Indole Carboxamides | |
| --- | --- |
| Example | Adhesion (% inhibition at given μM or IC$_{50}$, μM) |
| 26 | 29 |
| 29 | 43 |
| 30 | 34 |

[a]Chromium assay was used.

The compounds of the present invention, particularly of Formula III, have been found to inhibit the activation of the human immunodeficiency virus (HIV), latent in infected mammals, and therefore are useful in the treatment of AIDS.

Attempts at understanding the virologic and cellular basis for the clinical asymptomatic period reveal that HIV exists as a dormant or nonexpressing provirus in a reservoir population of chronically infected cells. A specific type of HIV, HIV-1, has been the subject of a number of different research projects which have shown that the virus exists as a dormant or nonexpressing provirus in a reservoir population of chronically infected T-lymphocytic cells. Greater detail concerning the nuclear and biochemical mechanisms responsible for maintaining the nonexpressive viral state, however, is beyond the scope of this review, but can be found in detail elsewhere. Mechanisms of HIV-1 Latency, Bednarik, et al., *AIDS* 1992;6:3–16.

Until recently, it was believed that HIV was dormant or nonexpressing in all the reservoir population of chronically infected cells during the clinical asymptomatic period. Observations of the low to absent levels of viraemia and virus replication in peripheral blood cells led to the impression that disease was not active during the clinical asymptomatic period. A team of scientists, however, have discovered that a true state of microbiological latency does not exist during the course of HIV infection. Fauci AS, et al., HIV Infection is Active and Progressive in Lymphoid Tissue During the Clinically Latent Stage of disease, *Nature* 1993;362:355–358.

The scientists reported a dichotomy between the levels of viral burden and virus replication in peripheral blood versus lymphoid organs during clinical latency. Based on these findings, therefore, the scientists have discovered that "peripheral blood does not accurately reflect the actual state of HIV disease, particularly early in the clinical course of HIV infection. In fact, HIV disease is active and progressive even when there is little evidence of disease activity by readily measured viral parameters in the peripheral blood, and the patient is experiencing clinical latency."

Inevitably, the disease state of HIV progresses from the clinically latent asymptomatic period to the expressive and active symptomatic period. Through the use of several different models, an understanding of the cellular pathways involved in HIV activation from laboratory latency has begun to unfold. According to Butera, et al., *AIDS* 1992;6:994, many of the cellular models of latency can be induced to express HIV-1 upon treatment with cytokines. This indicates that in the state of microbiologic latency, HIV-1 awaits an extracellular stimulus before initiating replication. This signal not only can be mediated though a soluble cytokine interaction with its receptor, but also through receptor-receptor interactions which occur during cell to cell communication or cellular stress such as UV light exposure and heat shock. Furthermore, an extracellular induction signal can be generated in an autocrine or paracrine fashion so that an HIV-1 activated cell can propagate its own expression while activating a nearby latent cell.

Additional factors have been considered by those of skill in the art to be involved in the activation of HIV. One study has shown that 12-O-tetradecanoylphorbol-13-acetate (TPA) mediates CD4 down regulation and viral expression in HIV-infected cells. Hamamoto, et al., *Biochem, Biophys. Res. Commun.* 1989;164:339–344. Interestingly, Hamamoto also examined the effect of the potent protein kinase C inhibitors staurosporine, H-7, and UCN-01 on TPA-mediated CD4 down regulation and augmentation of HIV expression. Staurosporine was found to be an effective TPA inhibitor for both of these actions.

The cellular pathways involved in mediating the activating signal from the plasma membrane to the integrated virus, resulting in HIV-1 expression, are much less clear. Recently, the development of a reliable and simple system for evaluating compounds that could prevent activation of latent HIV was reported at the National Cooperative Discovery Grant (NCDDG)/AIDS by P. Feorino, S. T. Butera, T. M. Folks, and R. F. Schinazi, Nov. 3–7, 1991. The assay system employed the OM-10.1 cell line, a unique chronically-infected promyelocytic clone which remains CD4+ until HIV-1 activation with tumor necrosis factor-α. The expression of CD4+ on the cell surface and the activity of reverse transcriptase are used as markers for quantitating viral expression. Alternatively, other HIV markers, such as protease activity, which are known to those of skill in the art can be used. OM-10.1 cells remain CD4+ until viral activation and respond to tumor necrosis factor induction, and therefore, these cultures are used to conveniently and rapidly examine pharmacologics for an ability to prevent CD4+ down modulation (decrease in expression of CD4+ on the cell surface) and HIV-1 expression.

A variety of compounds known to have antiviral properties against either acutely or chronically infected cells were evaluated for their ability to inhibit HIV expression in these OM-10.1 cells. Several compounds that interact with biochemical pathways that may interfere with the reactivation process were also examined. The results of the evaluation were presented in a poster at the NCDDG/AIDS, San Diego, Calif., Nov. 3–7 (1991). Among some 48 compounds evaluated, 3'-fluoro-3'-deoxythymidine (FLT), interferon Y, and desferrioxamine were considered modest inhibitors of the activation of HIV-1.

A representative compound of Formula III, 5-methoxy-1-methyl-3-(1-methylethoxy)-1H-indole-2-carboxamide showed an $IC_{50}$ of 0.8 $\mu$M inhibition in OM-10.1 cells.

The compounds of the present invention may be prepared by the following methods.

As starting materials, 3-hydroxy indole esters (1, Scheme I) are known or are readily prepared by known methods, such as: Unangst PC, et al., *J. Heterocyclic Chem.* 1987;24:811 and Moyer MP, et al., *J. Org. Chem.* 1986;51:5106. The hydroxy esters 1 are alkylated with an alkyl halide or sulfate in the presence of a base, such as potassium tert-butoxide or 1,8-diazobicyclo[5.4.0]undec-7-ene in acetone, acetonitrile, or methyl sulfoxide at 0°–80° C. to yield alkoxy esters 2. Saponification of the esters 2 by standard methods, such as heating with sodium or potassium hydroxide in water or an alcohol-water mixture, yields carboxylic acids 3. Reaction of 3 with ammonium hydroxide or an amine, such as methylamine, in the presence of a coupling agent, such as 1,1'-carbonyldiimidazole or dicyclohexylcarbodiimide, in acetonitrile or tetrahydrofuran at 0°–80° C. gives the amides 4. Alternately, acids 3 can be converted to acyl chlorides with thionyl chloride or oxalyl chloride in toluene or tetrahydrofuran at 0°–100° C., followed by reaction with an amine to yield amides 4.

In addition, esters 2 can be directly converted to the amides 4 by reaction with lithium amide in liquid, ammonia or tetrahydrofuran-liquid ammonia mixture at −78° C.–25° C.

Starting indoles containing a 3-thio substituent (5, Scheme II) are known or are readily prepared by known methods, such as: Unangst PC, et al., *J. Heterocyclic Chem*, 1987;24:817 and Atkinson JG, et al., *Synthesis* 1988;480. Thio-substituted esters 5 are converted to the corresponding carboxylic acids 6 and amides 7 by the methods described for the alkoxy esters in Scheme I.

Starting indoles containing a 3-amino substituent (8, Scheme III) are similarly known or are readily prepared by known methods, such as: Simakov SV, et al., *Khim.-Farm. ZU.* 1983;17:1183. Reaction of 8 with an aldehyde or ketone and sodium cyanoborohydride in acetic acid at 0°–80° C. gives the substituted amino esters 9. Preparation of 9 is also possible by alkylation of 8 with an alkyl halide and base, such as sodium bicarbonate, in a polar solvent, such as N,N-dimethylformamide or 1,3-dimethyl-2-imidazolidinone. Substituted amino esters 9 are converted to the corresponding carboxylic acids 10 and amides 11 by the methods described for the alkoxy esters in Scheme I.

SCHEME I

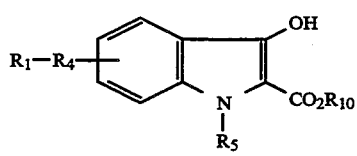

1

-continued
SCHEME I
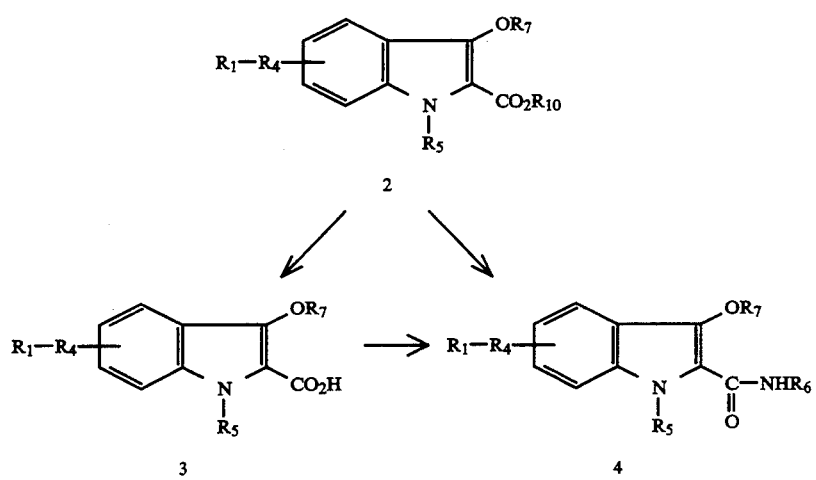
SCHEME II
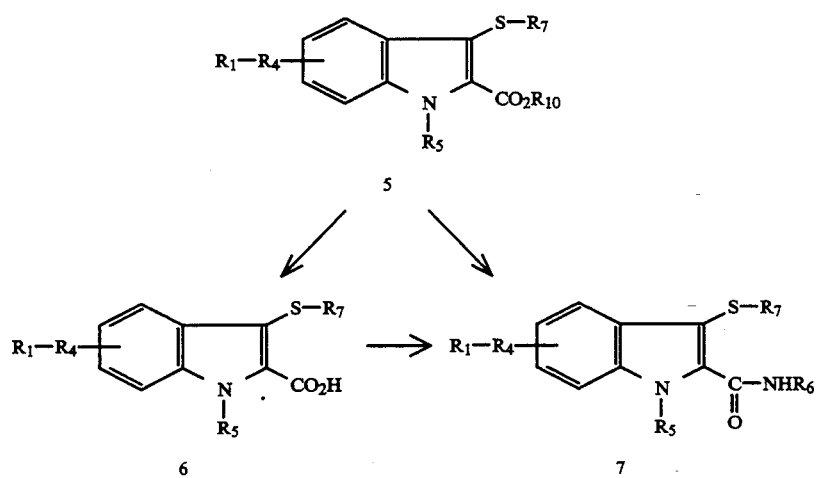
SCHEME III
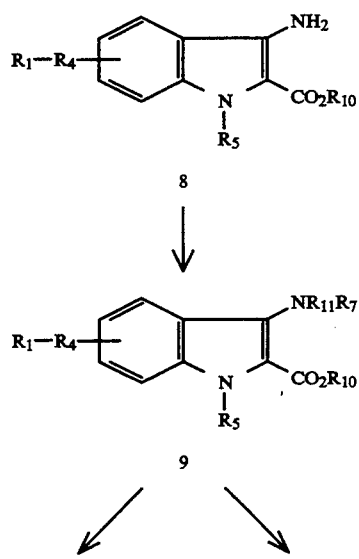

SCHEME III

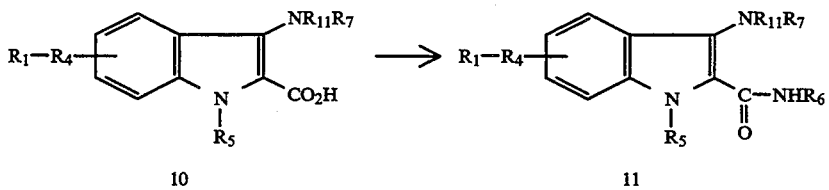

The following examples are illustrative of the preparation of the compounds of the present invention.

EXAMPLE 1

5-Methoxy-1-methyl-3-(1-methylethoxy)-1H-indole-2-carboxamide

A mixture of 5-methoxy-1-methyl-3-(1-methylethoxy)-1H-indole-2-carboxylic acid (4.0 g, 15 mmol; Unangst PC, et al., *J. Med. Chem.* 1989;32:1360) and 1,1'-carbonyldiimidazole (2.6 g, 16 mmol) in 75 mL of acetonitrile is stirred at reflux for 2 hours. The mixture is cooled slightly and 75 mL of concentrated ammonium hydroxide is added. After stirring for 15 minutes, the mixture is added to 600 g of ice and water. The precipitated solid is filtered, washed with water, and recrystallized from aqueous acetonitrile to give 2.1 g (53%) of product; mp 147°–149° C.

EXAMPLE 2

N,1-Dimethyl-5-methoxy-3-(1-methylethoxy)-1H-indole-2-carboxamide

Prepared from 5-methoxy-1-methyl-3-(1-methylethoxy)-1H-indole-2-carboxylic acid by the procedure of Example 1 with 40% aqueous methylamine solution substituted for ammonium hydroxide. Yield 45% after recrystallization from hexane; mp 85°–86° C.

EXAMPLE 3

Methyl 5-methoxy-3-(methylthio)-1H-indole-2-carboxylate

A mixture of methyl 5-methoxy-1H-indole-2-carboxylate (8.3 g, 40 mmol; Blaikie KG, Perkin WH Jr, *J. Chem. Soc.* 1924;125:296) and dimethyl sulfoxide (4.0 mL, 4.4 g, 56 mmol) in 75 mL of methanol is cooled in ice and treated with gaseous HCl. The temperature of the reaction mixture increases to 45° C. as the HCl is added. Additional HCl is added intermittently and the rate of cooling is adjusted so that a reaction temperature of 40°–50° C. is maintained for 3 hours. The mixture is cooled and the precipitated solid filtered and washed with ether to yield 6.3 g (52%) of [5-methoxy-2-(methoxycarbonyl)-1H-indol-3-yl] dimethylsulfonium chloride suitable for further synthesis; mp 130° C.-dec.

A suspension of the above salt product (8.3 g, 8 mmol) in 50 mL of N,N-dimethylformamide is immersed in an oil bath preheated to 120° C. The mixture is occasionally stirred as the solid gradually dissolves over 10 minutes. The cooled reaction mixture is added to 500 g of ice and water, and the precipitated solid is filtered and washed with 25% methanol-water to yield 6.1 g (88%) of product, suitable for further synthesis. A sample recrystallized from aqueous acetonitrile has mp 128°–130° C.

EXAMPLE 4

Methyl 5-methoxy-1-methyl-3-(methylthio)-1H-indole-2-carboxylate

A suspension of 60% sodium hydride in mineral oil (0.30 g, 7.5 mmol) in 3.0 mL of N,N-dimethylformamide is cooled in ice while a solution of methyl 5-methoxy-3-(methylthio)-1H-indole-2-carboxylate (1.3 g, 5.2 mmol) in 10 mL of N,N-dimethylformamide is added dropwise. The mixture is stirred for 45 minutes, then iodomethane (0.50 mL, 1.1 g, 8.0 mmol) is added in one portion. After stirring at room temperature for 8 hours, the mixture is added to 100 g of ice and water. The solid is filtered and washed with 10% methanol-water to yield 1.2 g (88%) of product. A sample purified by flash chromatography (silica gel, 25% hexane in dichloromethane elution) and recrystallized from hexane has mp 89°–91° C.

EXAMPLE 5

5-Methoxy-1-methyl-3-(methylthio)-1H-indole-2-carboxylic acid

A suspension of methyl 5-methoxy-1-methyl-3-(methylthio)-1H-indole-2-carboxylate (3.2 g, 12 mmol) in 65 mL of methanol is treated with a solution of potassium hydroxide (2.5 g, 45 mmol) in 25 mL of water. The mixture is stirred at reflux for 2 hours, then cooled and added to 400 g of ice and water. After washing with dichloromethane, the aqueous layer is stirred with celite filter-aid and filtered. The filtrate is acidified with 4.0N HCl and the precipitated solid is filtered and washed with 10% methanol-water to yield 2.6 g (87%) of product. A sample recrystallized from hexane-ethyl acetate has mp 165° C.-dec.

EXAMPLE 6

5-Methoxy-1-methyl-3-(methylthio)-1H-indole-2-carboxamide

Prepared from 5-methoxy-1-methyl-3-(methylthio)-1H-indole-2-carboxylic acid by the procedure of Example 1. Yield 58% after recrystallization from aqueous acetonitrile; mp 204°–206° C.

EXAMPLE 7

N, 1-Dimethyl-5-methoxy-3-(methylthio)-1H-indole-2-carboxamide

Prepared from 5-methoxy-1-methyl-3-(methylthio)-1H-indole-2-carboxylic acid by the procedure of Example 1 with 40% aqueous methylamine solution substituted for ammonium hydroxide. Yield 45% after recrystallization from ethyl acetate-hexane; mp 137°–139° C.

EXAMPLE 8

Ethyl 3-bromo-1-methyl-5-(phenylmethoxy)-1H-indole-2-carboxylate

A solution of ethyl 1-methyl-5-(phenylmethoxy)-1H-indole-2-carboxylate (60.9 g, 197 mmol; Monge Vega A, et al., *An. Quim.* 1976;72:267) in 550 mL of pyridine is cooled in ice and treated dropwise with a solution of pyridinium bromide perbromide (67.0 g, 209 mmol) in 200 mL of pyridine. The cooling bath is removed, and the mixture is stirred for 16 hours, then added to 4.0 L of cold water. The precipitated solid is filtered, washed with water, and recrystallized from ethyl acetate-hexane to give 58.4 g (76%) of product; mp 125–127° C.

EXAMPLE 9

3-Bromo-1-methyl-5-(phenylmethoxy)-1H-indole-2-carboxylic acid

A solution of potassium hydroxide (17.0 g, 303 mmol) in 3.0 L of 50% aqueous methanol is treated with ethyl 3-bromo-1-methyl-5-(phenylmethoxy)-1 H-indole-2-carboxylate (55.4 g, 143 mmol). The mixture is stirred at reflux for 5 hours, than decanted while warm from any insoluble material into 600 mL of hot water. The warm solution is quickly acidified with 100 mL of 4.0N HCl. An additional 1.0 L of cold water is added, and the mixture is stirred for 1 hour. The precipitated solid is filtered, stirred in 1.0 L of 25% methanol-water, and refiltered, to give 49.6 g (96%) of product, suitable for further synthesis. A sample recrystallized from aqueous acetonitrile has mp 210° C.-dec.

EXAMPLE 10

1,1-Dimethylethyl 3-bromo-1-methyl-5-(phenylmethoxy)-1H-indole-2-carboxylate

A suspension of 3-bromo-1-methyl-5-(phenylmethoxy)-1H-indole-2-carboxylic acid (43.0 g, 119 mmol) in 500 mL of toluene is heated in an oil bath at 85°–90° C. while N,N-dimethylformamide di-tert-butyl acetal (115 mL, 98 g, 480 mmol) is added dropwise. Heating is continued for 2 hours, and the cooled reaction mixture is filtered and diluted with fresh toluene. The solution is washed with brine, 5% aqueous sodium bicarbonate solution, and brine again, then dried (anhydrous sodium sulfate) and evaporated. Recrystallization of the residue from hexane yields 36.6 g (74%) of product; mp 97°–99° C.

EXAMPLE 11

1,1-Dimethylethyl 3-hydroxy-1-methyl-5-(phenylmethoxy)-1H-indole-2-carboxylate

A solution of 1,1-dimethylethyl 3-bromo-1-methyl-5-(phenylmethoxy)-1H-indole-2-carboxylate (18.6 g, 45 mmol) in 200 mL of tetrahydrofuran is cooled to −78° C. in a dry ice-acetone bath and treated dropwise with a solution of 1.6M n-butyl lithium in hexane (29 mL, 46 mmol). After 15 minutes a solution of trimethyl borate (5.2 mL, 4.8 g, 46 mmol) in 25 mL of tetrahydrofuran is added dropwise. The mixture is stirred for 1 hour, and 4.0 mL of acetic acid is slowly added. The mixture is stirred for an additional 10 minutes, and a solution of 30% hydrogen peroxide in water (5.4 mL, 1.8 g, 53 mmol) is slowly added. After 30 minutes, an additional 4.5 mL (1.5 g, 44 mmol) of peroxide solution is added, and the mixture is stirred at room temperature for 20 hours. The mixture is added to 1.0 L of water and extracted with ethyl acetate. The combined organic layers are washed with brine, 5% aqueous sodium bicarbonate solution, and brine again, then dried (anhydrous sodium sulfate) and evaporated to an oil residue. Purification of the residue by flash chromatography (silica gel, 50% dichloromethane in hexane elution) gives 8.2 g (52%) of product suitable for further synthesis. A sample recrystallized from hexane has mp 101°–103° C.

EXAMPLE 12

1-Dimethylethyl 1-methyl-(1-methylethoxy)-5-(phenylmethoxy)-1H-indole-2-carboxylate A solution of potassium tert-butoxide (4.0 g, 36 mmol) in 20 mL of dimethyl sulfoxide is treated dropwise with a solution of 1,1-dimethylethyl-3-hydroxy-1-methyl-5-(phenylmethoxy)-1H-indole-2-carboxylate (8.2 g, 23 mmol) in 200 mL of dimethyl sulfoxide. After 45 minutes 2-bromopropane (4.0 mL, 5.2 g, 43 mmol) is added, the mixture is stirred at room temperature for 18 hours, and an additional 3.5 mL (4.6 g, 37 mmol) of 2-bromopropane is added. After stirring for an additional 24 hours, the reaction mixture is added to a solution of 1.0 L of water, 250 mL of methanol, and 6.0 mL of acetic acid. The crude solid product is filtered and washed with 25% methanol in water. Purification of the crude product by flash chromatography (silica gel, elution with 33% hexane in dichloromethane) gives 5.6 g (61%) of product, suitable for further synthesis. A sample recrystallized from aqueous 2-propanol has mp 113°–115° C.

EXAMPLE 13

1-Methyl-3-(1-methylethoxy)-5-(phenylmethoxy)-1H-indole-2-carboxylic acid

A suspension of 1,1-dimethylethyl 1-methyl-3(1-methylethoxy)-5-(phenylmethoxy)-1H-indole-2-carboxylate (5.6 g, 14 mmol) in 80 mL of 2-methoxyethanol is treated with a solution of 50% aqueous sodium hydroxide (5.0 g, 63 mmol) followed by the addition of 15 mL of water. The mixture is stirred at reflux for 3 hours, then cooled and added to 700 mL of water. The mixture is heated on a hot plate until nearly one phase and filtered hot. The warm filtrate is immediately treated with 50 mL of 4.0N HCl. After cooling to room temperature, followed by 1 hour in an ice bath, the precipitated solid is filtered and washed with 25% methanol in water to give 4.2 g (88%) of product suitable for further synthesis. A sample recrystallized from ethyl acetate-hexane has mp 136° C.-dec.

EXAMPLE 14

1-Methyl-3-(1-methylethoxy)-5-(phenylmethoxy)-1H-indole-2-carboxamide

Prepared from 1-methyl-3-(1-methylethoxy)-5-(phenylmethoxy)-1H-indole-2-carboxylic acid by the procedure of Example 1. Yield 52% after recrystallization from ethyl acetate-hexane; mp 164°–166° C.

EXAMPLE 15

5-Hydroxy-1-methyl-3-(1-methylethoxy)-1H-indole-2-carboxamide

A suspension of 1-methyl-(1-methylethoxy)-5-(phenylmethoxy)-1H-indole-2-carboxamide (2.1 g, 6.2 mmol) in 100 mL of methanol is hydrogenated using 0.5 g of 20% palladium on carbon catalyst. The catalyst is filtered and the filtrate evaporated. Recrystallization of the residue from aqueous acetonitrile gives. 0.87 g (58%) of product; mp 234°–237° C.

EXAMPLE 16

5-Methoxy-3-(1-methylethoxy)-1-phenyl-1H-indole-2-carboxamide

A solution of 5-methoxy-3-(1-methylethoxy)-1-phenyl-1H-indole-2-carboxylic acid (3.3 g, 10 mmol; Unangst PC, et al., *J. Med. Chem.* 1989;32:1360) and a few drops of N,N-dimethylformamide in 50 mL of tetrahydrofuran is treated dropwise with oxalyl chloride (0.90 mL, 1.3 g, 10 mmol). The mixture is stirred at room temperature for 16 hours, and then the solvent is removed under vacuum. The residue is redissolved in fresh tetrahydrofuran and evaporated several times. The final crude acyl chloride residue is dissolved in 20 mL of tetrahydrofuran and the solution is added dropwise to 125 mL of concentrated ammonium hydroxide cooled in ice. The solid is filtered, washed with water, and recrystallized from ethyl acetate-hexane to yield 2.1 g (65%) of product; mp 152°–154° C.

EXAMPLE 17

N-(2-Hydroxyphenyl)-5-methoxy-3-(1-methylethoxy)-1-phenyl-1H-indole-2-carboxamide The procedure described in Example 16 is used to prepare the acyl chloride of 5-methoxy-3-(1-methylethoxy)-1-phenyl-1H-indole-2-carboxylic acid (4.0 g, 12 mmol). A solution of the crude acyl chloride in 45 mL of tetrahydrofuran is cooled in ice and treated dropwise with a solution of 2-aminophenol (1.3 g, 12 mmol) in 20 mL of tetrahydrofuran, followed by dropwise addition of triethylamine (1.7 mL, 1.2 g, 12 mmol). The mixture is stirred at room temperature for 2 hours and added to 300 mL of water. The mixture is extracted with dichloromethane, and the combined organic layers are washed with brine, dried (anhydrous sodium sulfate), and evaporated. Trituration of the residue with tert-butyl methyl ether yields 3.5 g (69%) of product; mp 168°–170° C.

EXAMPLE 18

5-Methoxy-3-(1-methylethoxy)-1H-indole-2-carboxamide

Lithium amide in liquid ammonia is prepared as described by Unangst PC and Carethers ME, *J. Heterocyclic Chem.* 1984;21:709, from lithium metal ribbon (0.059 g, 8.5 mmol). A solution of methyl 5-methoxy-3-(1-methylethoxy)-1H-indole-2-carboxylate (0.15 g, 0.57 mmol; Unangst PC, et al., *J, Heterocyclic Chem.* 1987;24:811) in 4.0 mL of tetrahydrofuran is added dropwise. The mixture is stirred for 1 hour and the excess ammonia is allowed to evaporate. The residue is diluted with ethyl acetate, and the organic layer is washed with 1.0N HCl brine, saturated sodium bicarbonate solution, and brine again. The solution is dried (anhydrous magnesium sulfate) and evaporated. Recrystallization of the residue from ethyl acetatehexane gives 0.11 g (76%) of product; mp 138.5°–140° C.

EXAMPLE 19

3-Ethoxy-5-methoxy-1-phenyl-1H-indole-2-carboxamide

A mixture of 3-ethoxy-5-methoxy-1-phenyl-1H-indole-2-carboxylic acid (0.11 g, 0.35 mmol; Unangst PC, et al., *J. Med. Chem.* 1989;32:1360) and 1,1'-carbonyldiimidazole (0.065 g, 0.40 mmol) in 5.0 mL of tetrahydrofuran is stirred at reflux for 90 minutes. The mixture is cooled slightly and 5.0 mL of concentrated ammonium hydroxide is added. After stirring for an additional 90 minutes, the mixture is partitioned between ethyl acetate and brine. The organic layer is washed several times with fresh brine, dried (anhydrous sodium sulfate) and evaporated. Recrystallization of the residue from ethyl acetate-hexane yields 0.082 g (75%) of product; mp 143°–144° C.

EXAMPLE 20

3-(Diethylamino)-5-methoxy-1H-indole-2-carboxamide, monohydrochloride

Prepared from ethyl 3-(diethylamino)-5-methoxy-1H-indole-2-carboxylate (Unangst PC, et al., *J. Heterocyclic Chem.* 1987;24:817) and lithium amide by the procedure described in Example 18, with the exception that dilute acetic acid is substituted for 1.0N HCl during the wash of the ethyl acetate extracts. The crude product is purified by flash chromatography (silica gel, 30% ethyl acetate in dichloromethane elution) to give a foam. The foam is dissolved in ether and treated with gaseous HCl to provide the product salt in 36% yield after recrystallization from acetonitrile; mp 244° C.-dec.

EXAMPLE 21

Ethyl 1-methyl-3-[(1-methylethyl)sulfinyl]-5-(phenylmethoxy)-1H-indole-2-carboxylate A slurry of ethyl 1-methyl-5-(phenylmethoxy)-1H-indole-2-carboxylate (10.0 g, 32 mmol; Monge Vega A, et al., *An. Ouim.* 1976;72:267) in 30 mL of chloroform is treated dropwise with thionyl chloride (9.5 mL, 15.5 g, 130 mmol). After stirring for 20 minutes, 90 mL of hexane is added, and stirring is continued for 30 minutes. The crude indole sulfinyl chloride intermediate is filtered, washed with hexane, and dissolved in 200 mL of tetrahydrofuran. The solution is cooled to −78° C. and treated dropwise with a 2.0M solution of isopropylmagnesium chloride in ether (16.4 mL, 32.8 mmol). After stirring for 15 minutes, the reaction mixture is quenched by the dropwise addition of 20 mL of 2.0N HCl. The reaction mixture is warmed to room temperature, diluted with water, and extracted with ethyl acetate. The combined organic layers are washed with brine, dried (anhydrous magnesium sulfate), and evaporated. The residue is triturated with ether to give a solid which is recrystallized from aqueous methanol to yield 6.8 g (53%) of product; mp 142°–145° C.

EXAMPLE 22

Ethyl 1-methyl-3-[(1-methylethyl)thio]-5-(phenylmethoxy)-methoxy-1H-indole-2-carboxylate A mixture of ethyl 1-methyl-3-[(1-methylethyl)sulfinyl]-5-(phenylmethoxy)-1H-indole-2-carboxylate (0.50 g, 1.3 mmol) and sodium iodide (0.69 g, 4.6 mmol) in 30 mL of tetrahydrofuran is cooled to 0° C. and treated dropwise with trifluoroacetic anhydride (1.0 mL, 1.5 g, 7.1 mmol). The mixture is stirred for 10 minutes, then quenched by pouring into 100 mL of cold 5% aqueous sodium bicarbonate solution. The mixture is extracted with ether, and the combined organic layers are washed with 5% aqueous sodium thiosulfate solution, followed by brine. The organic layer is dried (anhydrous magnesium sulfate) and evaporated to give 0.44 g (92%) of product; mp 94°–96° C.

EXAMPLE 23

1-Methyl-3-[(1-methylethyl)thio]-5-(phenylmethoxy)-1H-indole-2-carboxamide

Prepared from ethyl 1-methyl-3-[(1-methylethyl)thio]-5-(phenylmethoxy)-1H-indole-2-carboxylate and lithium amide as described in Example 18. After evaporation of excess ammonia, the residue is treated with ice water. The insoluble material is filtered and washed with water, then recrystallized from ethyl acetate-hexane. Yield 78%; mp 151°–154° C.

EXAMPLE 24

Methyl 5-methoxy-1-methyl-3-[(1-methylethyl)sulfinyl]-1H-indole-2-carboxylate

Prepared from methyl 5-methoxy-1-methyl-1H-indole-2-carboxylate (Trummlitz G, et al., U.S. Pat. No. 4,137,313) and thionyl chloride as described in Example 21. The crude product is purified by flash chromatography (silica gel, 30% ethyl acetate in hexane elution) to yield the final product. Yield 29%; mp 130°–134° C.

EXAMPLE 25

Methyl 5-methoxy-1-methyl-3-[(1-methylethyl)thio]-1H-indole-2-carboxylate

Prepared from methyl 5-methoxy-1-methyl-3-[(1-methylethyl)sulfinyl]-1H-indole-2-carboxylate by the procedure described in Example 22. The crude product is purified by flash chromatography (silica gel, 10% ethyl acetate in hexane elution). Yield 70% after recrystallization from ethyl acetate-hexane; mp 93°–95° C.

EXAMPLE 26

5-Methoxy-1-methyl-3-[(1-methylethyl)thio]-1H-indole-2-carboxamide

Prepared from methyl 5-methoxy-1-methyl-3-[(1-methylethyl)thio]-1H-indole-2-carboxylate and lithium amide as described in Example 23. Yield 68% after recrystallization from ethyl acetate-hexane; mp 122°–124° C.

EXAMPLE 27

Ethyl 5-hydroxy-1-methyl-1H-indole-2-carboxylate

Prepared from ethyl 1-methyl-5-(phenylmethoxy)-1H-indole-2-carboxylate (Monge Vega A, et al., *An. Ouim.* 72:267) by catalytic hydrogenolysis in ethanol as described in Example 15. Recrystallization from ether gives the product in 80% yield; mp 140°–142° C.

EXAMPLE 28

Ethyl 5-(acetyloxy)-1-methyl-1H-indole-2-carboxylate

A solution of ethyl 5-hydroxy-1-methyl-1H-indole-2-carboxylate (2.2 g, 10.0 mmol) in 50 mL of tetrahydrofuran is treated dropwise with acetyl chloride (0.80 mL, 0.88 g, 11.3 mmol) followed by triethylamine (1.6 mL, 1.2 g, 11.5 mmol). The mixture is stirred at room temperature for 16 hours, then diluted with water and extracted with ethyl acetate. The combined organic layers are washed with brine, dried (anhydrous magnesium sulfate), and evaporated. Recrystallization of the residue from ether-pentane gives 2.0 g (77%) of product; mp 87°–89° C.

EXAMPLE 29

5-Hydroxy-1-methyl-3-[(1-methylethyl)thio]-1H-indole-2-carboxamide

A solution of ethyl 5-(acetyloxy)-1-methyl-1H-indole-2-carboxylate (1.0 g, 3.8 mmol) in 10 mL of dichloromethane in treated with thionyl chloride and isopropylmagnesium chloride as described in Example 21. The crude product is purified by flash chromatography (silica gel, 20% ethyl acetate in hexane elution) to yield 0.51 g (38%) of intermediate ethyl 5-(acetyloxy)-1-methyl-3-[(1-methylethyl)sulfinyl]-1H-indole-2-carboxylate as a waxy solid.

A solution of the above sulfoxide intermediate (0.82 g, 2.3 mmol) in 20 mL of acetone is treated with sodium iodide and trifluoroacetic anhydride as described in Example 22. The crude product is purified by flash chromatography (silica gel, 10% ethyl acetate in hexane elution) to give 0.40 g (51%) of intermediate ethyl 5-(acetyloxy)-1-methyl-3 [(1-methylethyl)thio]-1H-indole-2-carboxylate as a solid of mp 60°–62° C., suitable for further synthesis.

A solution of the above ester intermediate (0.37 g, 1.1 mmol) in 3.0 mL of tetrahydrofuran is reacted with lithium amide as described in Example 18. After evaporation of excess ammonia, the residue is diluted with water and acidified with 2.0N HCl. The mixture is extracted with ethyl acetate. The combined organic layers are washed with brine, dried (anhydrous magnesium sulfate), and evaporated. The residue is purified by flash chromatography (silica gel, 20% ethyl acetate in hexane elution) followed by recrystallization from ethyl acetate-hexane to yield 0.22 g (76%) of product; mp 213°–215° C.

EXAMPLE 30

5-Methoxy-1-methoxymethyl-3-(1-methylethoxy)-1H-indole-2-carboxamide

5-Methoxy-3-(1-methylethoxy)-1H-indole-2-carboxamide (106 mg, 0.43 mmol) in 4 mL of dimethylformamide is added to a suspension of sodium hydride (60% by weight) (30 mg, 0.75 mol) in 2 mL of dimethylformamide. After 1 hour chloromethyl methyl ether (60 μL, 0.79 mmol) is added, and the solution is stirred at room temperature overnight. The reaction mixture is diluted with ethyl acetate and washed with brine. The organic layer is dried over MgSO$_4$. Filtration followed by concentration in vacuo and subsequent chromatography eluting with 1:1 ethyl acetate:hexane gives 40 mg of 5-methoxy-1-methoxymethyl-3-(1-methylethoxy)-1H-indole-2-carboxamide. An analytical sample was obtained by recrystallization from ethyl acetate:hexane; mp 145°–147° C.

EXAMPLE 31

1-Ethoxymethyl-5-methoxy-3-(1-methylethoxy)-1H-indole-2-carboxamide

5-Methoxy-3-(1-methylethoxy)-1H-indole-2-carboxamide (328 mg, 1.32 mmol) in 5 mL of dimethylformamide is added to a suspension of sodium hydride (60% by weight) (67 mg, 1.67 mol) in 5 mL of dimethylformamide. After 1.5 hours the mixture is cooled to 0° C. and chloromethyl ethyl ether (160 μL, 1.72 mmol) is added dropwise, and the solution is stirred at 0° C. for 20 minutes and then at room temperature for 1.5 hours. The reaction mixture is diluted with 1:1 hexane:ethyl acetate and washed with brine. The organic layer is dried over MgSO$_4$, filtered, and concentrated in vacuo. Chromatography eluting with 1:1 ethyl acetate:hexane gives 240 mg (51%) of 1-ethoxymethyl-5-methoxy-3-(1-methylethoxy)-1H-indole-2-carboxamide; mp 110°–112° C.

We claim:
1. A method of treating inflammatory diseases comprising administering to a mammal in need of treatment an antiinflammatory effective amount of a compound of the formula

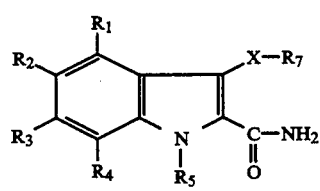

wherein R$_1$, R$_2$, R$_3$, and R$_4$ are each independently hydrogen, hydroxy, halogen, lower alkyl, lower alkoxy, benzyloxy, nitro, or —NR$_8$R$_9$, in which R$_8$ and R$_9$ are each independently hydrogen or lower alkyl;

$R_5$ is hydrogen, lower alkyl, phenyl, or —$CH_2OR_{10}$ in which $R_{10}$ is lower alkyl;

$R_7$ is lower alkyl, phenyl, or benzyl;

X is $S(O)_n$ or $NR_{11}$ in which n is 0, 1, or 2 and $R_{11}$ is hydrogen, lower alkyl, phenyl, or benzyl, or a pharmaceutically acceptable acid addition salt thereof, excluding 5-methoxy-3-(methylthio)-1H-indole-2-carboxamide.

2. The method of claim 1, employing a compound wherein $R_1$, $R_3$, and $R_4$ are hydrogen;

$R_2$ is hydroxy, lower alkoxy, or benzyloxy;

$R_5$ is hydrogen, lower alkyl, or phenyl; and $R_7$ is lower alkyl.

3. The method of claim 1, employing a compound selected from the group consisting of 5-methoxy-1-methyl-3-(methylthio)-1H-indole-2-carboxamide, 3-(diethylamino)-5-methoxy-1H-indole-2-carboxamide, 1-methyl-3-[(1-methylethyl)thio]-5-(phenylmethoxy)-1H-indole-2-carboxamide, 5-methoxy-1-methyl-3-[(1-methylethyl)thio]-1H-indole-2-carboxamide, and 5-hydroxy-1-methyl-3-[(1-methylethyl)thio]-1H-indole-2-carboxamide.

4. A method of treating inflammatory diseases comprising administering to a mammal in need of treatment an antiinflammatory effective amount of a compound of the formula

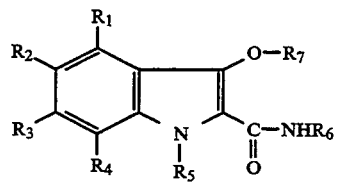

wherein $R_1$, $R_2$, $R_3$, and $R_4$ are each independently hydrogen, hydroxy, halogen, lower alkyl, lower alkoxy, benzyloxy, nitro, or —$NR_8R_9$, in which $R_8$ and $R_9$ are each independently hydrogen or lower alkyl;

$R_5$ is hydrogen, lower alkyl, phenyl, or —$CH_2OR_{10}$ in which $R_{10}$ is lower alkyl;

$R_6$ is hydrogen, lower alkyl, or benzyl;

$R_7$ is lower alkyl, phenyl, or benzyl, or a pharmaceutically acceptable acid addition salt thereof.

5. A method of claim 4, employing a compound wherein $R_1$, $R_3$, and $R_4$ are hydrogen, $R_2$ is hydroxy or lower alkoxy;

$R_5$ is hydrogen, lower alkyl, or phenyl;

$R_6$ is hydrogen; and $R_7$ is lower alkyl.

6. The method of claim 4, employing a compound selected from the group consisting of 5-methoxy-1-methyl-3-(1-methylethoxy)-1H-indole-2-carboxamide, 5-hydroxy-1-methyl-3-(1-methylethoxy)-1H-indole-2-carboxamide, 5-methoxy-3-(1-methylethoxy)-1-phenyl-1H-indole-2-carboxamide, 5-methoxy-3-(1-methylethoxy)-1H-indole-2-carboxamide, 3-ethoxy-5-methoxy-1-phenyl-1H-indole-2-carboxamide, 5-methoxy-3-(1-methylethoxy)-1-methoxymethyl-1H-indole-2-carboxamide, and 1-ethoxymethyl-5-methoxy-3-(1-methylethoxy)-1H-indole-2-carboxamide.

* * * * *